United States Patent
Swift et al.

(10) Patent No.: US 8,066,132 B2
(45) Date of Patent: Nov. 29, 2011

(54) WATER BOTTLE SYSTEM FOR USE IN A DENTAL OPERATORY

(75) Inventors: Ronald L. Swift, Medina, MN (US); James Michael Campion, Buffalo, MN (US)

(73) Assignee: Zirc Company, Buffalo, MN (US)

( * ) Notice: Subject to any disclaimer, the term of this patent is extended or adjusted under 35 U.S.C. 154(b) by 1194 days.

(21) Appl. No.: 11/821,337

(22) Filed: Jun. 21, 2007

(65) Prior Publication Data

US 2008/0318182 A1    Dec. 25, 2008

(51) Int. Cl.
*B65D 41/06* (2006.01)

(52) U.S. Cl. ........ 215/332; 215/331; 220/298; 220/304; 220/254.8

(58) Field of Classification Search ............... 215/44, 215/329, 330, 331, 332, 352, 309, 311, 315, 215/388, 389; 220/298, 304, 254.8, 705, 220/706, 709, 717; 116/228
See application file for complete search history.

(56) References Cited

U.S. PATENT DOCUMENTS

| 3,143,803 | A | | 8/1964 | Lune |
|---|---|---|---|---|
| 3,371,817 | A | * | 3/1968 | Gasbarra et al. ............... 220/298 |
| 3,718,973 | A | | 3/1973 | Slater et al. |
| 6,079,589 | A | * | 6/2000 | Matsuyama et al. .......... 220/715 |
| 6,250,920 | B1 | | 6/2001 | Overmyer |
| 6,375,024 | B1 | * | 4/2002 | Park ............................. 215/262 |
| 6,406,294 | B1 | | 6/2002 | Bell |
| 2003/0160020 | A1 | * | 8/2003 | Oh ................................ 215/330 |
| 2003/0230575 | A1 | * | 12/2003 | Laurent ....................... 220/254.8 |

* cited by examiner

*Primary Examiner* — Anthony Stashick
*Assistant Examiner* — James N Smalley
(74) *Attorney, Agent, or Firm* — David George Johnson

(57) ABSTRACT

A water bottle adapter (6) fits securely onto a water bottle (1) which is used to isolate the water within the bottle from a common water supply. The adapter (6) is fastened to a mating device by means of a threaded neck (7). The neck (7) includes two longitudinal tensioning ribs (37) that promote a retaining function between the neck (7) and any device that has been affixed to the neck (7). A pressure relief valve (13) having a valve stem (14) is formed within the lid (8) of the adapter (6) to permit the escape of air from the bottle (1) when in use. A series of ribs (19) is formed within a bore containing the valve stem (14) to dampen noise produced by the operation of the valve (13).

4 Claims, 4 Drawing Sheets

WATER BOTTLE SYSTEM FOR USE IN A DENTAL OPERATORY

FIELD OF THE INVENTION

The present invention relates generally to the field dental equipment, and more particularly to an improved water container.

BACKGROUND OF THE INVENTION

The typical dental lounge or chair includes a source of clean water and sometimes other liquids as well. The water is used to irrigate, rinse and cleanse a patient's mouth during most dental procedures. The water must be sanitary and is supplied to a variety of dental instruments through various conduits within or adjacent to the dental chair. Frequently the supply of water has been provided directly from the building water main. An example of such a system is disclosed in U.S. Pat. No. 3,143,803, entitled DENTAL LOUNGE UNIT, issued on May 11, 1962 to Lunn. The use of multiple chemicals complicates matters as multiple reservoirs must be filled, accesses by means of valves, pressurized and periodically cleaned. The inherent complexity of such a system is illustrated in U.S. Pat. No. 3,718,973, entitled DENTAL SYSTEM, issued on Mar. 6, 1973 to Slater et al.

As dental technology has progressed the sanitation of such systems has been questioned and the requirement for cleaning dental instrumentation has become more urgent. The use of multiple solution reservoirs and permanent conduit supply systems requires elaborate cleaning procedures. An example of such a device is disclosed in U.S. Pat. No. 6,250,920, entitled PURGE SYSTEM FOR FLUSHING AND DISINFECTING DENTAL UNITS, issued on Jun. 26, 2001 to Overmyer.

In order to improve and simplify operatory cleanliness, systems involving large liquid reservoirs and elaborate valve and conduit paths have given way to the widespread use of bottled water and other dental solutions. By placing the water or solution in a bottle not only is cleanliness improved, but the dental chair and its associated equipment may be readily moved within the operatory without the need to connect to a central water supply line or reservoir system. An example of such a bottled water system is disclosed in U.S. Pat. No. 6,406,294, entitled SELF CONTAINED DENTAL CHAIR WITH INTEGRATED COMPRESSOR AND VACUUM PUMP AND METHODS, issued on Jun. 18, 2002 to Bell.

Use of bottled water has, however, proved problematical in practice. First, most bottles are interconnected to the dental instrumentation via a threaded coupling. Typically, the bottle opening or neck is threaded and can be screwed directly onto or into the coupling. The bottle is usually in a vertical orientation and the coupling is rigidly affixed to the dental chair or an adjacent panel, requiring the user to align the bottle with the coupling and rotate the bottle for a number of revolutions in order to create a water tight connection.

In order to reduce the number of times that a bottle must be changed during a given day or week, the bottles have tended to be large, heavy duty containers. A larger bottle tends to defeat the goal of sanitation insofar as the container, once breached for use, remains in the ambient environment for a longer period of time and thus subject to contamination. Further, such a container when filled with water becomes increasingly awkward to align and fasten to a fixed, threaded coupling. The use of a quick disconnect fitting has been implemented, but such fittings invariably mate with a standardized, relatively small diameter coupling which is subjected to relatively greater stresses since the quick disconnect coupling requires the application of some added impulse of force in order to accomplish the actual mating or disengagement of the quick disconnect feature.

Most bottles are constructed of a translucent material. Even if the bottles are constructed of an optically clear material, in use the bottles are usually shielded somewhat from the normal room illumination by a shelf or panel, and so determining the water level within the bottle is often a challenge. While direct examination of the bottle is usually sufficient to determine the water level, a casual glance or peripheral view is often not enough to alert the practitioner that the water level is low enough to require replacement of the bottle.

A need therefore exists for a water bottle system that permits the use of a relatively small bottle that may be quickly installed and removed without introducing large stresses on a fixed, small diameter coupling. Further, a simple and reliable means of determining the liquid level is required so that the contents of the smaller capacity bottle are not permitted to be completely consumed while performing a dental procedure.

SUMMARY OF THE INVENTION

The present invention is a container or bottle suitable for use in a dental operatory. The container includes a quick release adaptor that caps the bottle and provides a transition to the standardized threaded coupling present in most dental equipment panels. The adaptor can therefore be attached to the coupling for extended periods while the bottle itself is removed from the adaptor frequently. In this manner the stress and wear on the small diameter coupling is substantially reduced.

The bottle is formed with an enlarged opening or mouth to simplify filling. The opening has a diameter that is several times greater than the diameter of the coupling. The adaptor base which mates with the bottle opening is of a greater diameter than the opening, thereby creating a large diameter adaptor surface which is more easily gripped by a human hand. A series of tabs formed on the perimeter of the bottle opening engage a series of channels formed on the bottom surface of the adaptor. Rotation of the bottle through approximately ninety degrees with respect to the adaptor base causes the tabs to engage at least one stop formed at the end of each channel, thereby securing the adaptor to the container. A gasket is placed on a ledge within the opening to form a water tight seal once the adaptor is fully engaged.

A separate cap may be placed over the opening for use after filling and during transport to the adaptor. The cap may be removed and placed beneath the bottle to provide a more stable, larger surface area base that prevents the bottle from tipping. The bottom of the bottle is formed to include an orifice adapted to accept an air hose by which the contents of the container may be pressurized for delivery to various dental instruments. The bottom of the container is also formed to include an area of reduced thickness in order to define an area of first failure in the event that the bottle is over pressurized.

A ring or annulus supported by buoyant beads or spheres is placed within the container. The beads support the ring so that the entire ring and bead assembly floats at approximately the surface level of the liquid contained within the bottle. The beads are brightly colored so that they are easily observed through the transparent sidewalls of the bottle. The spheres extend beyond the perimeter of the ring so that only a point on the surface of each sphere may contact the container wall, thereby reducing the opportunity for the ring and bead assembly to become lodged or entrapped within the interior of the bottle.

DETAILED DESCRIPTION OF THE INVENTION

Figure 2:
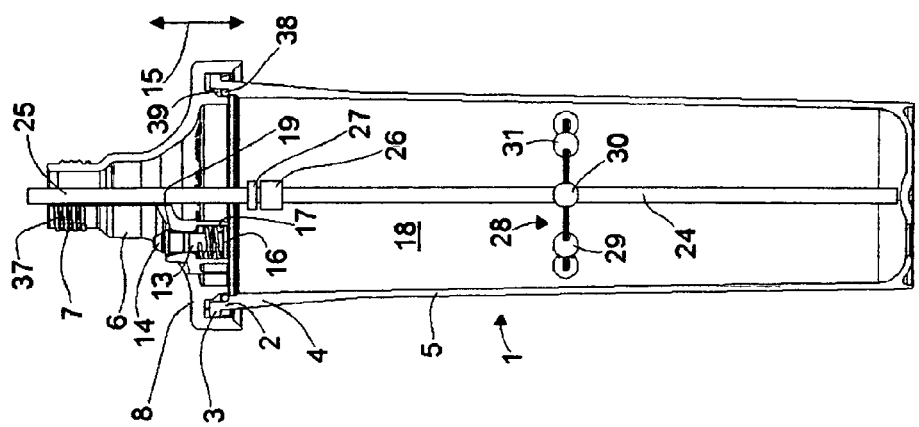
FIG. 2 is a side sectional view of the water bottle adapter taken along line 2-2 of FIG. 1.
Figure 1:
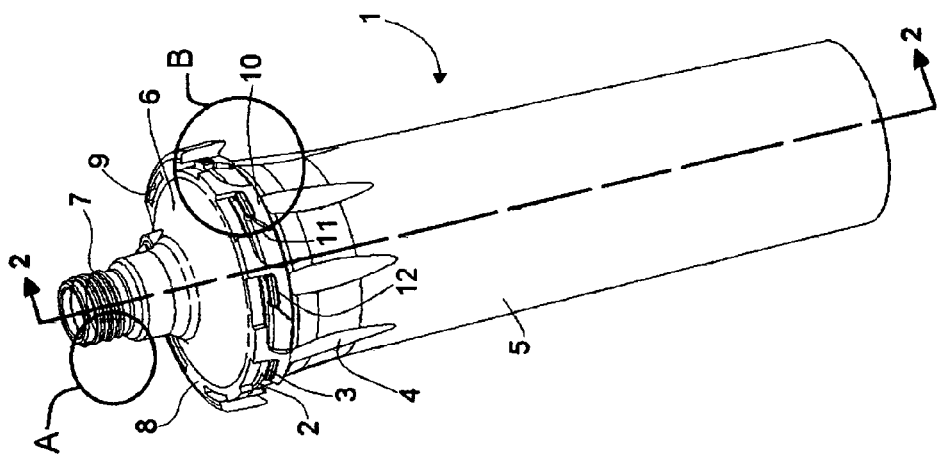
FIG. 1 is a perspective view of a water bottle adapter constructed according to the principles of the present invention and affixed to a water bottle.

FIGS. 1 and 2 illustrate a water bottle 1 which serves as a vessel for containing water. The bottle 1 is molded with a clear or lightly tinted material and is used to isolate water used on a dental or medical unit from a city or common water supply system in order to prevent the spread of bio-film contamination into the water supply. The bottle 1 typically has a capacity of one liter. The bottle 1 is formed to include an upper circumferential edge 2 from which protrude a number of circumferentially, equally spaced protrusions or latches 3. In a preferred embodiment of the present invention the protrusions are spaced at twenty two degree intervals around the edge 2 of the bottle 1. The bottle 1 is formed to include a series of buttresses 4 which are formed integrally with the bottle sidewall 5, each buttress 4 extending from an individual protrusion 3 and eventually tapering into the sidewall 5. The adapter 6 is formed to include a threaded neck 7 which may be mated with a standard threaded receptacle on an existing dental operatory unit. The neck 7 also includes two vertically extending tensioning ribs 37 which assist the neck in gripping the threads of any mating device (not shown) that is threaded onto the neck 7. The adapter 6 includes a lid 8 into which are formed a series of rectangular bores or recesses 9. The recesses 9 are spaced circumferentially around the lid 8 at approximately twenty two degree intervals and are dimensioned so as to engage the protrusions 3 in a secure, rigidly mated relationship. In particular, the resilient base 10 of each recess 9 includes an inclined shoulder 11 that urges the protrusion 3 into a notch 12 that secures the protrusion in place within the recess 9. An o-ring 38 is placed within cavity 39 of the lid 8. The o-ring is preferably formed of a No. 151 silicone material and functions as a pressure retaining seal to prevent leakage between the lid 8 and the bottle 1. The o-ring may be readily removed from the cavity 39 as needed in order to accomplish replacement or cleaning.

Figure 4:
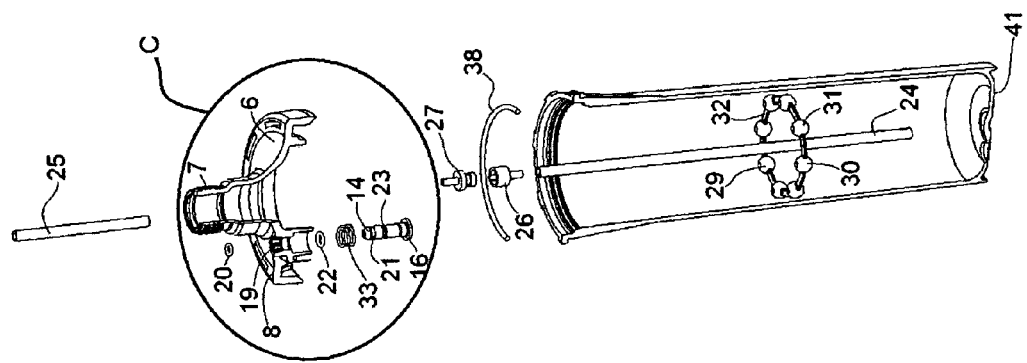
FIG. 4 is an exploded sectional view of the code ring assembly taken along line 2-2 of FIG. 1.
Figure 8:
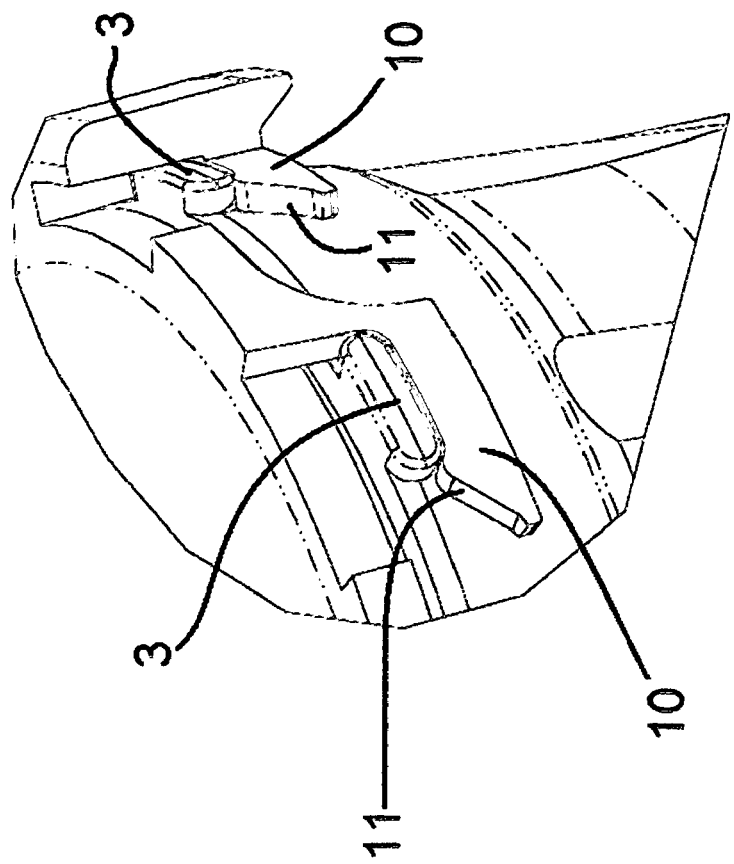
FIG. 8 is a detail view of region "B" as depicted in FIG. 1.
Figure 7:
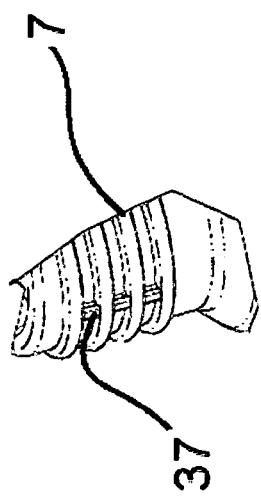
FIG. 7 is a detail view of region "A" as depicted in FIG. 1.
Figure 10:
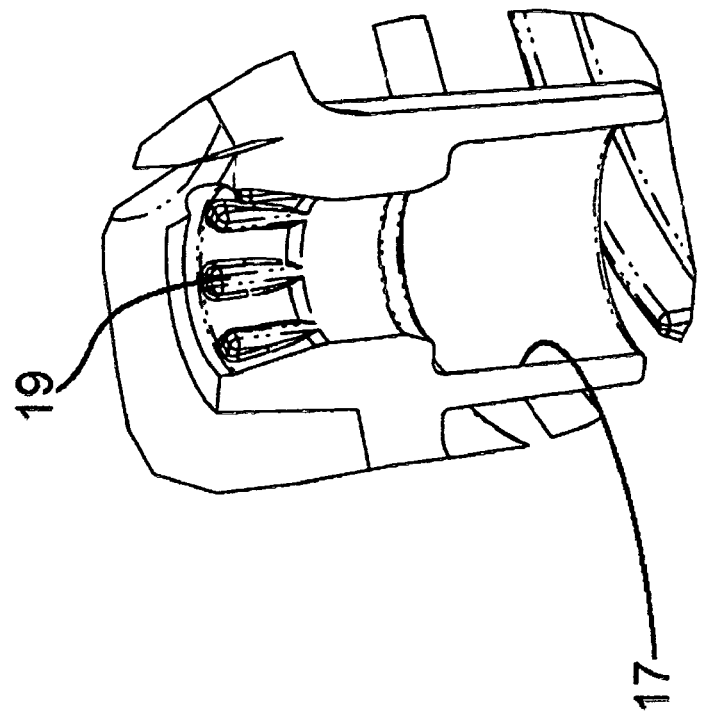
FIG. 10 is a detail view of region "D" as depicted in FIG. 9.
Figure 9:
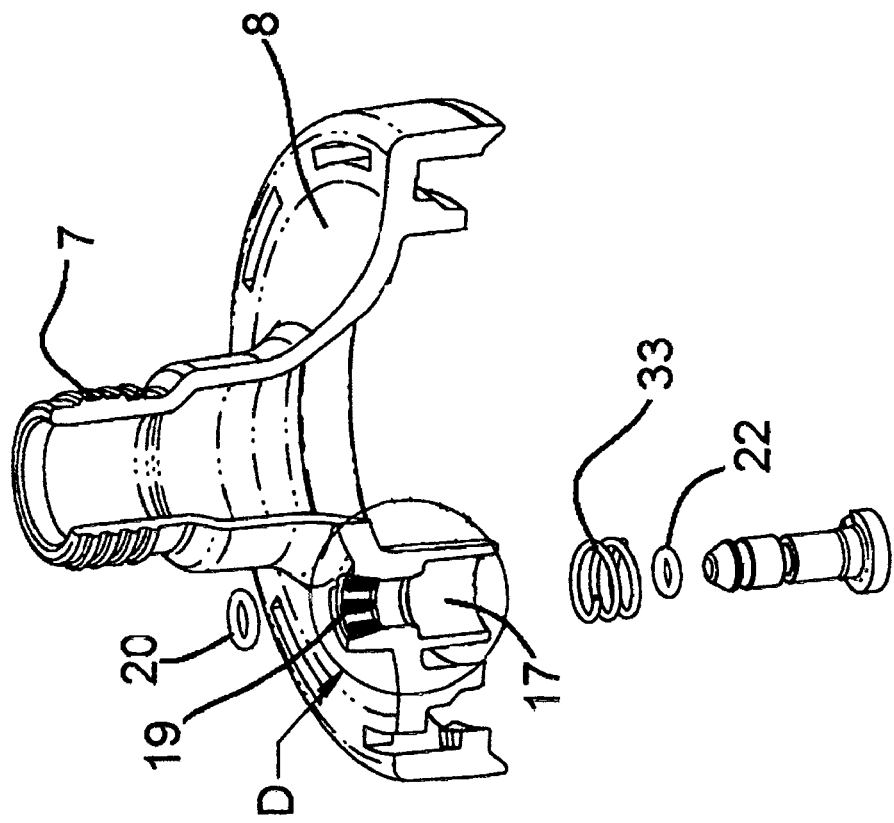
FIG. 9 is a detail view of region "C" as depicted in FIG. 4.

Referring also to FIG. 4, the adapter 6 is also seen to include a pressure relief valve 13. The valve 13 includes a stem 14 which is adapted to move upwardly or downwardly as indicated by the directions of arrows 15. The stem 14 is formed to include a substantially planar base 16 which resides within a cavity 17 that is formed integrally as part of the adapter 6. The dimensions and shape of the cavity 17 is such as to retain the base 16 within the cavity 17. A spring 33 biases the base 16, and hence the entire valve stem 14, in a downward direction. As pressure increases within the interior 18 of bottle 1, the bias of spring 33 is overcome and the base 16 lifts upwardly permitting air to escape past the valve stem 14. An o-ring 20 fits within groove 21 formed within the valve stem 14, which o-ring 22 fits within the groove 23. A series of ribs 19 is formed within the bore within which the valve stem 14 resides. The ribs 19 serve two purposes. The first purpose is to dampen the sound of air escaping past the valve stem 14, which can otherwise make an explosive popping noise. The second purpose is to assist in retaining the o-ring 20 within the groove 21.

Figure 3:
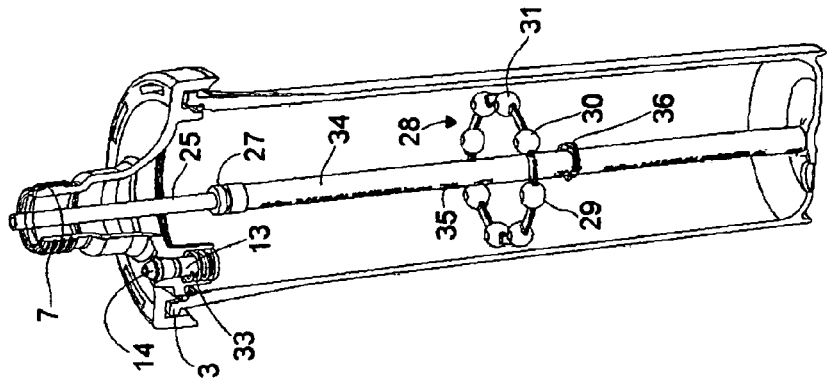
FIG. 3 is a perspective sectional view of the code ring assembly taken along line 2-2 of FIG. 1 in which a filter element has been substituted for the replacement tube.
Figure 5:
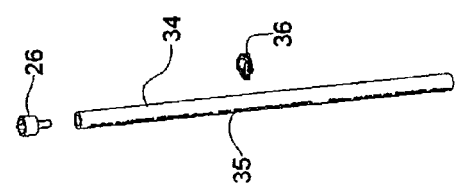
FIG. 5 is a perspective view of the date ring and filter assembly depicted in FIG. 3.

Also visible in FIG. 2 is the replacement tube 24 which provides a path for water to exit the interior 18 of bottle 1. Typically the bottle 1 is supplied to a dental or medical practitioner with some type of water evacuation tube 25. In order to permit use of the adapter 6 with a wide variety of bottles 1, a replacement tube 24 is supplied with the adapter 6. The tube 25 is cut to a length that will permit the replacement tube 24 to extend for approximately ninety percent of the height of the bottle 1. A male luer type fitting 26 is fitted to the replacement tube 24 while a female luer type fitting 27 is affixed to the original tube 25. Referring also to FIGS. 3 and 5, the replacement tube 24 has been removed and a disposable water filter 34 has been mated to the male luer fitting 27. The water filter 34 includes abbreviated date information 35, such as the first letter of each month, which can be marked with a clip 36, in order to indicate the date of installation or expiration of the filter 34. The water filter 34 is described more fully in U.S. Pat. No. 5,370,534, entitled "Water Purification System for Dental Equipment".

An additional item supplied with the adapter 6 is a bubble level indicator 28. The indicator 28 is formed to include a plurality of buoyant polypropylene bubbles 29, 30 and 31, for example, affixed to a ring 32. The bubbles 29-31 are preferably formed to have a bright color such as neon blue or neon yellow. The indicator 28 floats at the top surface of water residing within the bottle 1 and permits the level of water remaining within the bottle 1 to be easily determined from a distance with only a casual glance.

Figure 6:
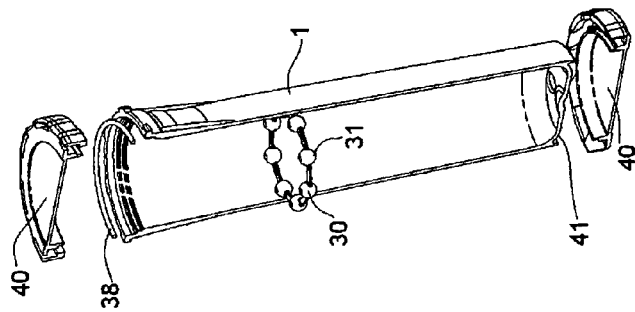
FIG. 6 is a perspective view of a lid and stand, shown as if viewed along section line 2-2 which may be used with the water bottle illustrated in FIG. 1.

Referring also to FIG. 6, a storage lid 40 is supplied to cover the bottle 1 when not in use or when the practitioner prepares particular solutions in advance or for reserve. The storage lid 40 may also be placed on the bottom 41 of the bottle 1 in order to serve as a bottle stand or as a convenient place of storage when the bottle 1 is otherwise in use.

From the foregoing one can readily foresee that numerous modifications to the foregoing may be made without departing from the spirit and the scope of the invention. For example, the lid 8 may be of any shape that is capable of securely mating with the bottle 1 and supporting the valve stem 14. The recesses 9 and protrusions 3 may have various alternate geometries while accomplishing the same interlocking task. The materials used to construct and form the present invention may be of any type that is compatible with a moist and sterile environment. Further, the shape and dimensions of the ribs 19 may be modified as necessary to accommodate a valve stem 14 having a different geometry. The claims define the scope of the invention.

We claim:

1. A water dispensing system including a bottle and an adaptor, wherein the adaptor comprises;

a threaded neck which may be mated to a threaded receptacle;

at least one tensioning rib extending longitudinally along the threaded neck;

a lid, the lid being adapted to mate with the water bottle, wherein the lid further comprises a pressure relief valve, the pressure relief valve residing within the lid, the valve providing fluid communication between an interior region of the bottle and a region exterior to the bottle such as an ambient atmosphere, wherein the pressure relief valve further comprises a valve stem, the valve stem residing within a bore formed within the lid, the bore tending to constrain movement of the valve stem to a direction that is substantially parallel to a longitudinal axis of the bottle; and a circumferential groove formed on an exterior surface of the valve stem;

a first o-ring, the first o-ring residing within the circumferential groove; and a spring, the spring residing with the bore, the spring tending to bias the valve stem in a direction causing the valve to be closed;

a second o-ring, the second o-ring residing between the lid and the bottle so as to prevent water from exiting a region between the lid and the bottle;

a plurality of substantially rectangular recesses formed within the lid at regular angular intervals, wherein the recesses are located at approximately twenty two degree intervals along a circumference of the lid;

a plurality of substantially rectangular protrusions formed so as to extend radially from a region of the bottle adjacent to the recesses such that a each of the protrusions resides within each of the recesses when the lid is securely affixed to the bottle;

at least one resilient base, each base extending from the lid to form a single recess;

an inclined shoulder formed at a distal end of each resilient base, the inclined shoulder tending to direct the protrusion into the recess that urges the protrusion as the lid is rotated about a longitudinal axis, wherein the resilient base member further comprises a notch, the notch residing adjacent to the inclined shoulder, the notch tending to retain the protrusion within the recess after rotation of the lid has caused the protrusion to travel beyond the inclined shoulder; and a plurality of longitudinally extending ribs formed within the bore, the ribs being in sliding contact with the valve stem so as to attenuate rapid movement of the valve stem.

2. The water dispensing system of claim 1, further comprising a water supply tube, the water supply tube extending longitudinally into an interior region of the bottle via the threaded neck;

a replacement tube, the replacement tube residing within the interior region of the tube, and a tube coupling, the tube coupling joining the water supply tube to the replacement tube in a substantially collinear relationship.

3. The water dispensing system of claim 2, further comprising a floating level indicator residing within the interior region of the bottle.

4. The water dispensing system of claim 3, further comprising a storage lid, the storage lid being adapted to seal the bottle when the bottle is not in use, the storage lid also being adapted to be affixed to a base region of the bottle and serve as a support stand for the bottle.

\* \* \* \* \*